US009728733B2

(12) United States Patent
Annunziata et al.

(10) Patent No.: US 9,728,733 B2
(45) Date of Patent: Aug. 8, 2017

(54) THIN FILM DEVICE WITH PROTECTIVE LAYER

(71) Applicant: International Business Machines Corporation, Armonk, NY (US)

(72) Inventors: Anthony J. Annunziata, Stamford, CT (US); Ching-Tzu Chen, Ossining, NY (US); Joel D. Chudow, Bronx, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/235,161

(22) Filed: Aug. 12, 2016

(65) Prior Publication Data
US 2016/0351679 A1    Dec. 1, 2016

Related U.S. Application Data

(62) Division of application No. 14/571,771, filed on Dec. 16, 2014.

(51) Int. Cl.
*H01L 21/441*    (2006.01)
*H01L 51/05*    (2006.01)
(Continued)

(52) U.S. Cl.
CPC ....... *H01L 51/0541* (2013.01); *G01N 27/414* (2013.01); *H01L 21/0254* (2013.01); *H01L 21/02527* (2013.01); *H01L 21/02568* (2013.01); *H01L 21/02606* (2013.01); *H01L 21/043* (2013.01); *H01L 21/283* (2013.01); *H01L 21/441* (2013.01); *H01L 29/0665* (2013.01); *H01L 29/0673* (2013.01);
(Continued)

(58) Field of Classification Search
None
See application file for complete search history.

(56) References Cited

U.S. PATENT DOCUMENTS 5,324,683 A    6/1994  Fitch et al.
6,928,879 B2   8/2005  Partridge et al.
(Continued)

OTHER PUBLICATIONS

Barrios, Carlos Angulo; "Optical Slot-Waveguide Based Biochemical Sensors"; Sensors; Published Jun. 16, 2009; 15 pgs.
(Continued)

*Primary Examiner* — Charles Garber
*Assistant Examiner* — Steven Christopher
(74) *Attorney, Agent, or Firm* — Edward J. Wixted, III

(57)    ABSTRACT

Embodiments of the invention include a method for fabricating a semiconductor device and the resulting structure. A substrate is provided. A plurality of metal portions are formed on the substrate, wherein the plurality of metal portions are arranged such that areas of the substrate remain exposed. A thin film layer is deposited on the plurality of metal portions and the exposed areas of the substrate. A dielectric layer is deposited, wherein the dielectric layer is in contact with portions of the thin film layer on the plurality of metal portions, and wherein the dielectric layer is not in contact with portions of the thin film layer on the exposed areas of the substrate such that one or more enclosed spaces are present between the thin film layer on the exposed areas of the substrate and the dielectric layer.

7 Claims, 2 Drawing Sheets

(51) Int. Cl.
  *H01L 29/786* (2006.01)
  *H01L 29/16* (2006.01)
  *H01L 29/06* (2006.01)
  *H01L 21/02* (2006.01)
  *H01L 21/283* (2006.01)
  *H01L 29/20* (2006.01)
  *H01L 29/24* (2006.01)
  *H01L 21/04* (2006.01)
  *H01L 51/00* (2006.01)
  *H01L 29/66* (2006.01)
  *H01L 29/778* (2006.01)
  *G01N 27/414* (2006.01)
  *H01L 43/08* (2006.01)
  *H01L 49/02* (2006.01)
  *H01L 23/532* (2006.01)
  *H01L 21/768* (2006.01)

(52) U.S. Cl.
  CPC ...... *H01L 29/1606* (2013.01); *H01L 29/2003* (2013.01); *H01L 29/24* (2013.01); *H01L 29/66045* (2013.01); *H01L 29/66969* (2013.01); *H01L 29/778* (2013.01); *H01L 29/78696* (2013.01); *H01L 51/0048* (2013.01); *H01L 51/0558* (2013.01); *H01L 21/7682* (2013.01); *H01L 23/53276* (2013.01); *H01L 28/60* (2013.01); *H01L 43/08* (2013.01); *H01L 2221/1094* (2013.01)

(56) References Cited

U.S. PATENT DOCUMENTS

| | | | |
|---|---|---|---|
| 7,301,199 B2 | 11/2007 | Lieber et al. | |
| 7,358,106 B2 | 4/2008 | Potter | |
| 7,361,991 B2 | 4/2008 | Saenger et al. | |
| 7,544,523 B2 | 6/2009 | Schwind et al. | |
| 7,855,435 B2 | 12/2010 | Klostermann et al. | |
| 7,902,820 B2 | 3/2011 | Vervaeke et al. | |
| 7,928,421 B2 | 4/2011 | Lung | |
| 7,943,480 B2 | 5/2011 | Edelstein et al. | |
| 7,968,433 B2 | 6/2011 | Nikoobakht | |
| 8,017,025 B2 | 9/2011 | Gaillard et al. | |
| 8,039,739 B1 | 10/2011 | Capps et al. | |
| 8,062,497 B2 | 11/2011 | Witvrouw et al. | |
| 8,119,020 B2 | 2/2012 | Ito et al. | |
| 8,148,179 B2 | 4/2012 | Aitken et al. | |
| 8,209,857 B2 | 7/2012 | Najafi et al. | |
| 8,222,795 B2 | 7/2012 | Sinha et al. | |
| 8,304,906 B2 | 11/2012 | Huang et al. | |
| 8,357,922 B2 | 1/2013 | Hong et al. | |
| 8,404,582 B2 | 3/2013 | Horak et al. | |
| 8,426,928 B2 | 4/2013 | van Wingerden et al. | |
| 8,435,604 B2 | 5/2013 | Aitken et al. | |
| 8,482,974 B2 | 7/2013 | Saito et al. | |
| 8,486,580 B2 | 7/2013 | Tucker et al. | |
| 8,487,511 B2 | 7/2013 | Sinha et al. | |
| 8,501,524 B2 | 8/2013 | Cho et al. | |
| 8,518,581 B2 | 8/2013 | Neudecker et al. | |
| 8,525,024 B2 | 9/2013 | Kaneda et al. | |
| 8,592,876 B2 | 11/2013 | Ding et al. | |
| 8,969,940 B1 | 3/2015 | Yater et al. | |
| 9,406,872 B1 | 8/2016 | Annunziata et al. | |
| 2009/0014885 A1 | 1/2009 | Chen et al. | |
| 2009/0239338 A1 | 9/2009 | Zhou et al. | |
| 2011/0026232 A1 | 2/2011 | Lin et al. | |
| 2012/0112152 A1 | 5/2012 | Bulovic et al. | |
| 2012/0231604 A1* | 9/2012 | Liu | H01L 27/101 438/382 |
| 2013/0214415 A1* | 8/2013 | Pachamuthu | H01L 21/7682 257/751 |
| 2014/0008611 A1 | 1/2014 | Geim et al. | |
| 2014/0145735 A1 | 5/2014 | Koester | |
| 2014/0197459 A1 | 7/2014 | Kis et al. | |
| 2014/0227861 A1* | 8/2014 | Wu | H01J 37/3211 438/468 |
| 2015/0287799 A1* | 10/2015 | Murashige | H01L 29/45 349/46 |
| 2015/0321215 A1 | 11/2015 | Huh et al. | |
| 2015/0323482 A1 | 11/2015 | Shimoyama et al. | |
| 2015/0364614 A1 | 12/2015 | Withers et al. | |
| 2016/0172507 A1 | 6/2016 | Annunziata et al. | |

OTHER PUBLICATIONS

Chen, et al.; "Low-damage high-throughput grazing-angle sputter disposition on graphene"; AIP Publishing; Jul. 16, 2013; 25 pgs.
Appendix P: List of IBM Patents or Patent Applications Treated as Related; Dated Aug. 12, 2016; pp. 1-2.
U.S. Appl. No. 15/183,172, filed Jun. 15, 2016; Entitled "Fabricating Two-Dimensional Array of Four-Terminal Thin Film Devices With Surface-Sensitive Conductor Layer".
U.S. Appl. No. 15/235,142, filed Aug. 12, 2016; Entitled "Thin Film Device With Protective Layer".

* cited by examiner

THIN FILM DEVICE WITH PROTECTIVE LAYER

BACKGROUND OF THE INVENTION

The present invention relates generally to the field of semiconductor devices and fabrication, and more particularly to the fabrication of a thin film device with a protective layer.

A topological insulator is a material with time reversal symmetry and non-trivial topological order that behaves as an insulator in its interior but whose surface contains conducting states, meaning that electrons can only move along the surface of the material.

Thin-film is a layer of material ranging from fractions of a nanometer (monolayer) to several micrometers in thickness. Electronic semiconductor devices are a main application benefitting from thin-film construction. A thin-film-transistor is a kind of transistor made by depositing thin films of an active semiconductor layer over a supporting, but non-conducting, substrate.

SUMMARY

Embodiments of the invention include a method for fabricating a semiconductor device and the resulting structure. The method can include providing a substrate. The method can also include forming a plurality of metal portions on the substrate, wherein the plurality of metal portions are arranged such that areas of the substrate remain exposed. The method can also include depositing a thin film layer on the plurality of metal portions and the exposed areas of the substrate. The method can also include depositing a dielectric layer, wherein the dielectric layer is in contact with portions of the thin film layer on the plurality of metal portions, and wherein the dielectric layer is not in contact with portions of the thin film layer on the exposed areas of the substrate such that one or more enclosed spaces are present between the thin film layer on the exposed areas of the substrate and the dielectric layer.

DETAILED DESCRIPTION

Figure 1:
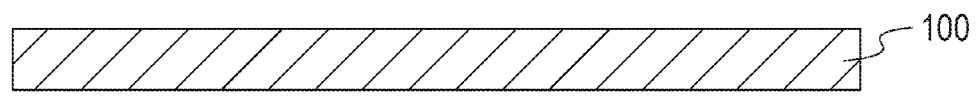
FIG. 1 depicts a semiconductor substrate upon which embodiments of the invention can be fabricated, in accordance with an embodiment of the invention.

Embodiments of the present invention recognize that device technologies based on ultra-thin films (e.g., graphene transistors or sensors, superconducting nanowire signal photon detectors, topological insulator materials used for sensors or logic devices) can be extremely sensitive to operating environments. Embodiments of the present invention recognize that electrical transport and/or detection can occur at or near the surface of a thin film, or within a thin film thickness, and that damage to the surface of such a thin film, or other effects from environmental exposure, can dramatically impact performance of a device. Further, embodiments of the present invention recognize that electrical contact is often needed at the edge or underneath a thin film layer within a device. Embodiments of the present invention describe structures and methods for creating a two-terminal protected device.

Detailed embodiments of the claimed structures and methods are disclosed herein; however, it is to be understood that the disclosed embodiments are merely illustrative of the claimed structures and methods that may be embodied in various forms. In addition, each of the examples given in connection with the various embodiments are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure.

References in the specification to "one embodiment," "an embodiment," "an example embodiment," etc., indicate that the embodiment described may include a particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "right," "left," "vertical," "horizontal," "top," "bottom," and derivatives thereof shall relate to the disclosed structures and methods, as oriented in the drawing Figures. The terms "overlaying," "atop," "positioned on," or "positioned atop" mean that a first element, such as a first structure, is present on a second element, such as a second structure, wherein intervening elements, such as an interface structure may be present between the first element and the second element. The term "direct contact" means that a first element, such as a first structure, and a second element, such as a second structure, are connected without any intermediary conducting, insulating or semiconductor layers at the interface of the two elements.

The present invention will now be described in detail with reference to the Figures.

FIG. 1 depicts a semiconductor substrate upon which embodiments of the invention can be fabricated. Semiconductor substrate 100 is preferably composed of a silicon (Si) containing material. Silicon containing materials include, but are not limited to, Si, single crystal Si, polycrystalline Si, silicon-germanium (SiGe), single crystal SiGe, polycrystalline SiGe, or Si doped with carbon (C), amorphous Si and combinations and multi-layers thereof. Semiconductor substrate 100 can also be composed of other semiconductor materials, such as Ge, and compound semiconductor substrates such as type III/V semiconductor substrates, e.g., gallium arsenide (GaAs). In general, semiconductor substrate 100 is a smooth surface substrate. In some embodiments (not shown), semiconductor substrate 100 can be a partially processed complementary metal-oxide-semiconductor (CMOS) integrated wafer with transistors and wiring levels or gate electrodes embedded beneath the surface.

Figure 2:
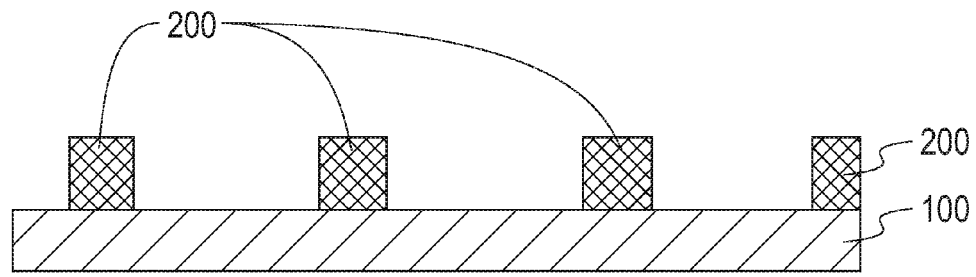
FIG. 2 depicts a process of forming a ribbed metal portion upon the semiconductor substrate, in accordance with an embodiment of the invention.

FIG. 2 depicts fabrication steps, in accordance with an embodiment of the present invention. FIG. 2 shows the portion of semiconductor substrate 100 shown in FIG. 1 with ribbed metal 200 formed on top of semiconductor substrate 100. Ribbed metal 200 can be formed upon substrate 100 via known techniques in the art. In one embodiment, ribbed metal 200 is formed using a photolithographic and subtractive etching process to define the structure of ribbed metal 200. Photolithography is a process to pattern parts of a thin film or the bulk of a substrate. For example, a metal layer can be initially formed on top of semiconductor substrate 100, and ribbed metal 200 may be the resulting metal of the metal layer, subsequent to etching away excess metal from the metal layer. Ribbed metal 200 can be composed of different types of metal, such as, but not limited to, copper, aluminum, gold, palladium or any other conductive material. In some embodiments, ribbed metal 200 has a nonmetallic, and/or nonconductive top layer. In general, individual ribs of ribbed metal 200 act as terminals for the resulting device (see FIGS. 4 and 5). In some embodiments, individual ribs of ribbed metal 200 act as a shunt between sections of the resulting device (see FIGS. 4 and 5) that are in contact with semiconductor substrate 100.

In some embodiments, each rib of ribbed metal 200 is of the same type of metal. In other embodiments, individual portions of ribbed metal 200 can be different types of metal. In some embodiments, individual portions of ribbed metal 200 are disposed on top of semiconductor substrate 100 in a periodic order. In other embodiments, individual portions of ribbed metal 200 are disposed on top of semiconductor substrate 100 in an aperiodic order.

In some embodiments, individual portions of ribbed metal 200 make electrical contact with a circuit, such as a readout circuit, located at the end of or beneath respective ribs. For example, each portion of ribbed metal 200 can be an elongated, rod-like member or structure that extends to, or near, the edge of semiconductor substrate 100 and can make electrical contact with a circuit located at the described location. In other embodiments, individual portions of ribbed metal 200 form islands on top of semiconductor substrate 100. In such an embodiment, individual portions of ribbed metal 200 can be connected to transistors through semiconductor substrate 100, such as, for example, when semiconductor substrate 100 is a partially processed CMOS-integrated wafer with transistors and wiring levels or gate electrode (not shown) beneath the surface of semiconductor substrate 100.

Figure 3:
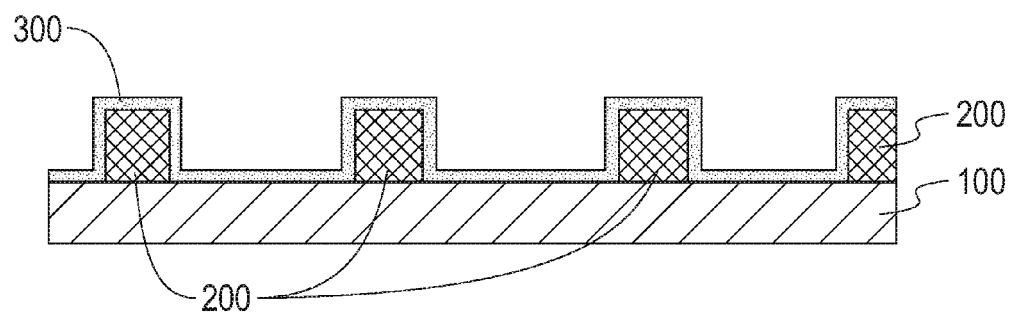
FIG. 3 depicts a process of depositing a thin film layer that acts as the active material for the device, in accordance with an embodiment of the invention.

FIG. 3 depicts additional fabrication steps, in accordance with an embodiment of the present invention. FIG. 3 illustrates a process of depositing a thin film layer, in accordance with one embodiment of the present invention. FIG. 3 shows the portion of semiconductor substrate 100 with ribbed metal 200, shown in FIG. 2, with thin film 300 formed on top of ribbed metal 200 and semiconductor substrate 100 in a conformal fashion. Thin film 300 can be, for example, a topological insulator, graphene, carbon nanotubes, transition metal dichalcogenide monolayers, hexagonal boron nitride, or boron nanotubes. Thin film 300 can be deposited via thin film deposition methods known in the art. The specific type of deposition method used to deposit thin film 300 can vary based upon the specific material(s) that comprise thin film 300. For example, thin film 300 can be deposited via direct transfer, spin coating, evaporation, sputtering, or other techniques known in the art, in accordance with the selected material of thin film 300, in accordance with the embodiment of the invention. While the depicted embodiment includes only thin film 300, it should be recognized that embodiments of the present invention recognize that a multi-layer thin film can be deposited, as desired for particular applications.

In some embodiments, a chemical or other type of surface preparation is used, or a seed layer is deposited. Such preparation can facilitate increased ohmic electrical contact between thin film 300 and ribbed metal 200.

In embodiments of the present invention, sections of thin film 300 located between individual ribs of ribbed metal 200 are considered active material for the device. In a two-terminal device application, an electrical current can be passed across the active material for the device, acting as a channel, from a first portion of ribbed metal 200, acting as a first terminal (e.g., a source), to a second portion of ribbed metal 200, acting as a second terminal (e.g., a drain). In embodiments of the present invention, portions of ribbed metal 200 act to shunt the bias current that would otherwise exist between the multiple sections of thin film 300 (e.g. a first section of thin film 300 between a first portion of ribbed metal 200 and a second portion of ribbed metal 200, and a second portion of thin film 300 between the second portion of ribbed metal 200 and a third portion of ribbed metal 200) that are in contact with semiconductor substrate 100. In some embodiments, the portion of thin film 300 that is considered the active material for the device is of a material that is extremely sensitive to environmental factors. In a thin film, such as thin film 300, electrical transport and/or detection occurs at or near the surface of the thin film. As such, damage to the surface of the thin film can impact the performance of the device.

Figure 4:
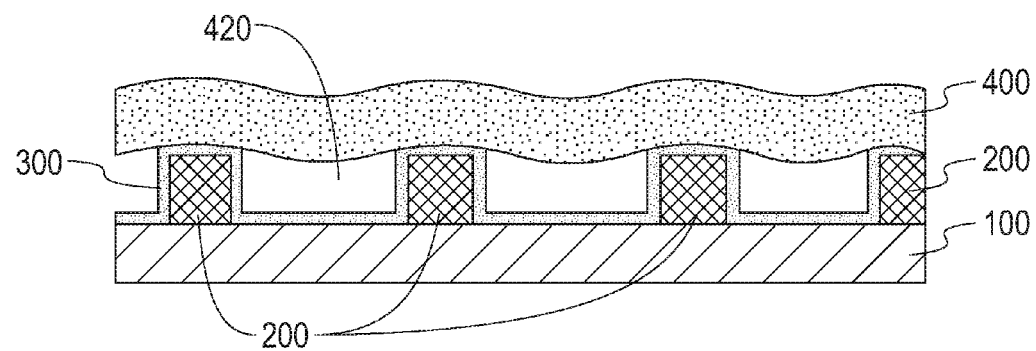
FIG. 4 depicts a process of depositing a capping layer, in accordance with an embodiment of the invention.

FIG. 4 depicts additional fabrication steps, in accordance with an embodiment of the present invention. FIG. 4 illustrates a process of depositing a capping layer, in accordance with one embodiment of the present invention. FIG. 4 shows the portion of semiconductor substrate 100 with ribbed metal 200, thin film 300, and capping layer 400. Capping layer 400 can be a dielectric material. For example, capping layer 400 can be oxide, nitride, silicon nitride, or any other dielectric material. In general, capping layer 400 is deposited such that at least one enclosed space, such as enclosed space 420, is created. In some embodiments, capping layer 400 is deposited in a non-conformal manner. In other embodiments, capping layer 400 is deposited in a semi-conformal manner. In some embodiments, capping layer 400 is deposited such that capping layer 400 contacts the top surface of portions of ribbed metal 200. In general, capping layer 400 is deposited such that capping layer 400 does not contact one or more portions of thin film 300 that are in contact with semiconductor substrate 100 and are between two portions of ribbed metal 200.

In some embodiments, capping layer 400 is deposited while the device is in a vacuum, or substantial vacuum. For example, capping layer 400 can be deposited while the device is in a vacuum chamber. In other embodiments, capping layer 400 is deposited while the device is exposed to an inert gas.

In an alternate embodiment, capping layer 400 is composed of a semi-permeable membrane acting as a selective filter. For example, polytetrafluoroethylene or carbon-fluorocarbon membranes provide selective gas species diffusion allowing for the transmission and subsequent detection of single gas molecules, such as nitrogen oxide, ammonia, or carbon dioxide. Ion-selective membranes, composed of materials such as valinomycin or polyvinylchloride, or size-selective caps, such as a cellulose-based dialysis membrane, can function as transporters of particular ions or allow transmission of only a restricted particle size range for biosensing applications.

In some embodiments, enclosed spaces, such as enclosed space 420, are vacuum pockets. Vacuum pockets that exist as enclosed spaces, such as enclosed space 420, act to protect the surface of portions of thin film 300 within the enclosed spaces (e.g., within enclosed space 420). In general, the vacuum pockets are substantially free of gases or other materials. Ideally, a vacuum pocket will be an enclosed space, such as enclosed space 420, which exists in a vacuum. In other embodiments, enclosed spaces, such as enclosed space 420, are filled with an inert gas, such as a noble gas (e.g., helium, neon, argon, krypton, xenon, or radon), or a compound gas, such as a compound gas containing argon. An inert gas can provide structural and/or chemical stability to the portions of thin film 300 within the enclosed spaces (e.g., within enclosed space 420). In general, enclosed spaces, such as enclosed space 420 protect the active material for the device from external environmental impurities and effects.

While the depicted embodiments show a cross section of semiconductor substrate 100, and the resulting fabricated device, it should be noted that embodiments of the present invention are structured such that enclosed spaces, such as enclosed space 420, may be present. In some embodiments, capping layer 400, or an additional layer, is deposited such that a hermetic seal is created at the edges (not shown) of semiconductor substrate 100.

The resulting structure is generally a protected surface-sensitive device utilizing the response of a thin film surface, such as a portion of thin film 300 in contact with semiconductor substrate 100 and located between a first metal portion and a second metal portion of ribbed metal 200. In some embodiments, the resulting structure is a two-terminal device. The resulting structure can be, for example, a magnetic sensing cell utilizing the response of a topological insulator in a magnetic field. In alternative embodiments, the resulting structure can be a graphene-based transistor or sensor, or a thin film capacitor.

Figure 5:
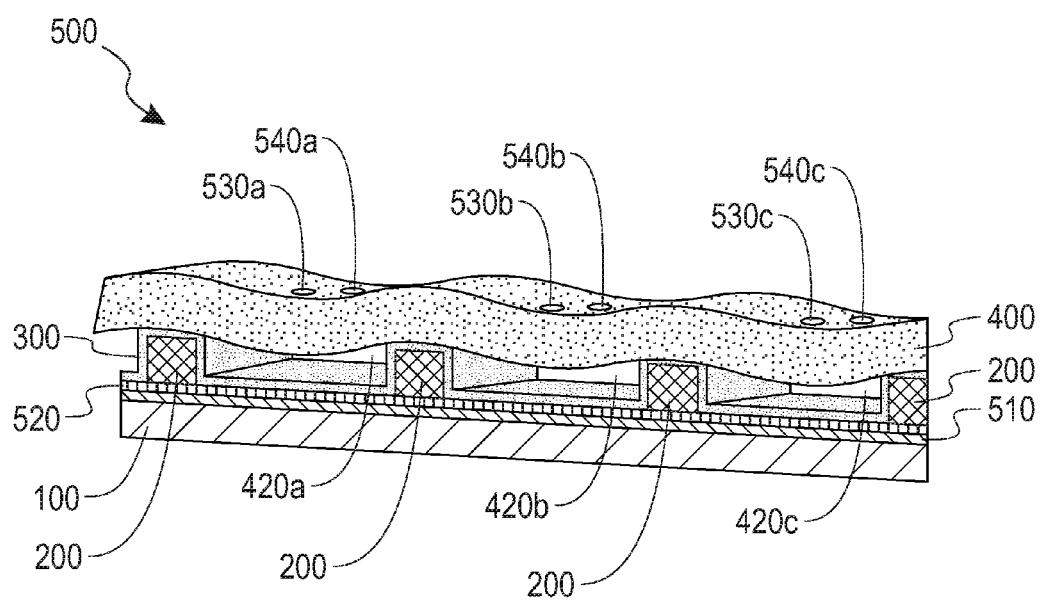
FIG. 5 depicts an embodiment of the invention for chemical sensing, in accordance with an embodiment of the invention.

FIG. 5 depicts an alternate structure, in accordance with an embodiment of the present invention. In the depicted embodiment, structure 500 can be, for example, a chemical sensor. In general, structure 500 includes one or more compartments (e.g., compartments 420a-c), each accessible via two openings (e.g., 530a-c, 540a-c). In some embodiments, one opening acts as an inlet to the compartment, while the other opening acts as an outlet. A specimen under test may be allowed to flow through one or more compartments via the inlet and the outlet for each respective compartment of the one or more compartments. In some embodiments, the specimen under test is a gas, for example, gas molecules, such as $NO_2$ or $CO_2$. In other embodiments, the specimen under test is a liquid. For example, for biosensing, the specimen under test could be a liquid containing ions, such as potassium in blood.

The fabrication of structure 500 is described with reference to the Figures. As described in reference to FIG. 1, semiconductor substrate 100 is provided.

In some embodiments, gate layer 510 is deposited on top of semiconductor substrate 100. In other embodiments (not shown), substrate 100 is gate layer 510. In general, gate layer 510 is a conductive material and forms the back gate of structure 500. Gate layer 510 can be, for example, highly doped silicon.

Dielectric layer 520 is deposited on top of gate layer 510. Dielectric layer 520 is generally a thin layer of insulating material. Dielectric layer 520 can be composed of, for example, hexagonal boron nitride (BN), $SiO_x$, $HfO_2$, $SiN_x$, or other insulating materials known in the art.

In general, ribbed metal 200, thin film 300, and capping layer 420 can be deposited or otherwise formed on top of dielectric layer 520. Ribbed metal 200, thin film 300, and capping layer 420 can be deposited or otherwise formed in the manner previously described with regard to FIGS. 2-4. However, in some embodiments, thin film 300 is deposited on top of dielectric layer 520, prior to forming ribbed metal 200, such that ribbed metal portion 200 is formed on top of thin film 300. In such an embodiment, a seed layer (not shown) can be deposited upon dielectric layer 520 to assist the deposition of thin film 300 on dielectric layer 520. In the depicted embodiment, thin film 300 can be composed of, for example, graphene, carbon nanotubes, or a topological insulator material. In some embodiments, thin film 300 is patterned into a nanoribben or nanomesh geometry, which may increase electrical sensitivity of the active material (e.g., a portion of thin film 300 in contact with dielectric layer 520 located between a first portion of ribbed metal 200 and a second portion of ribbed metal 200). In some embodiments, thin film 300 is annealed, passivated and/or functionalized for multichannel chemical sensing. Multiple compartments can exist, as defined by the arrangement of portions of ribbed metal 200, capping layer 400, and/or other layers (not shown) that can define the physical shape of each compartment. In the depicted embodiment, three compartments are shown: compartment 420a, compartment 420b, and compartment 420c. In some embodiments, portions of thin film 300 located within a specific compartment are functionalized with different sensitizing agents.

As described in reference to FIG. 4, capping layer 400 results in the creation of one or more enclosed spaces (e.g., enclosed space 420 of FIG. 4) defined by portions of ribbed metal 200. With regard to structure 500, two openings can be formed through capping layer 400 exposing one or more enclosed spaces. Each of the two openings can act as an inlet or an outlet to a compartment within structure 500. In the depicted embodiment, opening 530a and opening 540a are formed through capping layer 400 providing access to compartment 420a. Similarly, openings 530b and 540b provide access to compartment 420b, and openings 530c and 540c provide access to compartment 420c. While the depicted structure, structure 500, depicts three compartments, it shall be recognized that any number of compartments can exist, in accordance with embodiments of the present invention. In some embodiments, openings (e.g., 530a-c, 540a-c) are formed via an etching technique known in the art.

In other embodiments, compartments (e.g., 420a-c) can be formed by depositing a layer of sacrificial material prior to depositing capping layer 400. After depositing the layer of sacrificial material, capping layer 400 can be deposited, as described with reference to FIG. 4. Selective removal, and/or etching techniques, can then be used to remove portions of capping layer 400 and the sacrificial material to create compartments (e.g., 420a-c) and openings (e.g., 530a-c, 540a-c).

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Having described embodiments of a thin film device with a protective layer and a process of manufacturing a thin film device with a protective layer (which are intended to be illustrative and not limiting), it is noted that modifications and variations may be made by persons skilled in the art in light of the above teachings. It is therefore to be understood that changes may be made in the particular embodiments disclosed which are within the scope of the invention as outlined by the appended claims.

What is claimed is:

1. A method for fabricating a semiconductor device, the method comprising:
   providing a substrate;
   forming a plurality of metal portions on the substrate, wherein:
      the plurality of metal portions are arranged such that areas of the substrate remain exposed;
      a first metal portion of the plurality of metal portions acts as a source; and
      a second metal portion of the plurality of metal portions acts as a drain;
   depositing a thin film layer on the plurality of metal portions and the exposed areas of the substrate, wherein a portion of the thin film layer between the first metal portion and the second metal portion acts as a channel; and
   depositing a dielectric layer, wherein the dielectric layer is in contact with portions of the thin film layer on the plurality of metal portions, and wherein the dielectric layer is not in contact with portions of the thin film layer on the exposed areas of the substrate such that one or more enclosed spaces are present between the thin film layer on the exposed areas of the substrate and the dielectric layer.

2. The method of claim 1, wherein at least one metal portion of the plurality of metal portions is an elongated, rod-like member, and wherein the at least one metal portion acts as a terminal.

3. The method of claim 1, wherein the first metal portion is of a first type of metal and wherein the second metal portion is of a second type of metal.

4. The method of claim 1, wherein depositing the dielectric layer occurs within a vacuum chamber, such that the one or more enclosed spaces are a vacuum.

5. The method of claim 1, wherein the one or more enclosed spaces contain an inert gas.

6. The method of claim 1, wherein the thin film layer is composed of graphene.

7. The method of claim 1, wherein the thin film layer is deposited in a conformal manner upon exposed surfaces of the plurality of metal portions and the exposed areas of the substrate.

* * * * *